(12) United States Patent
Kobler et al.

(10) Patent No.: US 11,179,979 B2
(45) Date of Patent: Nov. 23, 2021

(54) VALVE FOR TUBELESS TIRES

(71) Applicant: SPORT COMPONENTS AG, Zürich (CH)

(72) Inventors: Pius Kobler, Zürich (CH); Dominik Eggert, Zürich (CH)

(73) Assignee: SPORT COMPONENTS AG, Zurich (CH)

( * ) Notice: Subject to any disclaimer, the term of this patent is extended or adjusted under 35 U.S.C. 154(b) by 0 days.

(21) Appl. No.: 16/694,443

(22) Filed: Nov. 25, 2019

(65) Prior Publication Data

US 2020/0086700 A1 Mar. 19, 2020

Related U.S. Application Data

(63) Continuation of application No. 15/120,005, filed on Aug. 18, 2016, now abandoned.

(51) Int. Cl.
| | |
|---|---|
| *B60C 29/00* | (2006.01) |
| *B60C 29/06* | (2006.01) |
| *F16K 15/14* | (2006.01) |
| *B60C 5/00* | (2006.01) |
| *F16K 15/20* | (2006.01) |
| B60C 25/00 | (2006.01) |
| B60C 25/05 | (2006.01) |
| G01N 33/26 | (2006.01) |
| B60C 5/12 | (2006.01) |

(52) U.S. Cl.
CPC ............ *B60C 29/005* (2013.01); *B60C 5/004* (2013.01); *B60C 29/002* (2013.01); *B60C 29/062* (2013.01); *F16K 15/147* (2013.01); *F16K 15/202* (2013.01); B60C 5/12 (2013.01); B60C 25/005 (2013.01); B60C 25/0551 (2013.01); B60C 25/0554 (2013.01); B60C 2200/12 (2013.01); G01N 33/26 (2013.01)

(58) Field of Classification Search
CPC ....... B60C 29/00; B60C 29/005; B60C 29/02; B60C 29/04
See application file for complete search history.

(56) References Cited

U.S. PATENT DOCUMENTS

| | | |
|---|---|---|
| 670,725 A | 3/1901 | Pickett |
| 2,064,695 A | 12/1936 | Sipe |
| 2,082,972 A | 6/1937 | Perry |
| 2,928,448 A | 3/1960 | Hosking |
| 3,007,483 A | 11/1961 | Keefe |

(Continued)

*Primary Examiner* — Jason R Bellinger
(74) *Attorney, Agent, or Firm* — Pauley Erickson & Swanson (57) ABSTRACT

The invention is directed to a valve stem system (1) for tubeless wheels. The valve stem system (1) includes a valve stem body (2) with a first end (3) and a second end (4), wherein the second end (4) is located in a tire/rim-volume when mounted at the wheel. A first valve (5) is arranged at the second end (4) of the valve stem body (2). The first valve (5) is a self-sealing one-way valve. A second valve (10) is removably mountable at the first end (3) and is, when mounted, at least partially housed in the valve stem body (2). The second valve (10) comprises a valve stem core inserted in the valve stem body (2) and can be added or removed from the valve stem body (2) while pressure is maintained within the tire by the first valve (5). The invention further concerns a probe (30) for a valve stem system, a method to test the amount of sealant in a wheel and a refilling assembly (80) for a wheel.

13 Claims, 7 Drawing Sheets

(56) References Cited

U.S. PATENT DOCUMENTS

| | | | |
|---|---|---|---|
| 3,442,316 | A | 5/1969 | McMaster |
| 3,465,780 | A | 9/1969 | Duymelinck et al. |
| 4,462,449 | A | 7/1984 | Zabel, Jr. |
| 5,012,954 | A | 5/1991 | Will |
| 5,479,975 | A | 1/1996 | Fogal, Sr. et al. |
| 5,694,969 | A | 12/1997 | DeVuyst |
| 2003/0032507 | A1 | 2/2003 | Lacroix et al. |
| 2006/0021472 | A1 | 2/2006 | Ragan et al. |
| 2017/0057309 | A1 | 3/2017 | Kobler et al. |
| 2018/0126963 | A1 | 5/2018 | Kobler et al. |
| 2020/0148177 | A1 | 5/2020 | Kobler et al. |

VALVE FOR TUBELESS TIRES

CROSS-REFERENCE TO RELATED APPLICATIONS

This application is a continuation of U.S. patent application Ser. No. 15/120,005, filed on 18 Aug. 2016, now abandoned. The parent application is hereby incorporated by reference herein in its entirety and is made a part hereof, including but not limited to those portions which specifically appear hereinafter.

BACKGROUND OF THE INVENTION

Field of the Invention

The present invention is directed to a valve stem system e.g. for bicycle wheels, in particular for tubeless wheels.

Discussion of Related Art

WO 2010/009887 relates to a device for filling air tires, particularly bicycle tires, with a tire sealing fluid through the valves of the tires. The device is configured as an adapter set having a connector for the tire fluid, and having multiple individual parts which can be inserted into one another, and onto the valves by means of inserting, clipping, and/or screwing, which can be varied with respect to one another depending on the valve type, such as Dunlop valves, Quick valves, or Sclaverand valves.

US 2006/0021472 relates to a device for injecting tire sealant fluid into a tire. A syringe type reservoir is connected to a long, flexible tube which is in turn connected to a valve stem connector. The valve stem connector has two different threads, Schrader and Presta, to accommodate both types of valve stems. The Schrader type threads are larger than the Presta type threads and thus the Presta type threads are positioned further into the valve stem connector. The larger Schrader type threads are used on automobiles and less expensive bicycles. The tire sealant injector can be used on bicycles, utility vehicles and even automobiles.

U.S. Pat. No. 4,462,449 by Zabel discloses a valve mechanism with a single valve having a single valve core comprising two sealing elements, which are an elastomeric member and a needle with head portion sealingly biased by spring means against the upper distal opening. Both sealing elements are integrally formed in one piece in the single valve core and can only be removed jointly. Both sealing elements are arranged in series to improve air tightness of the valve.

U.S. Pat. No. 2,064,695 by Sipe discloses an air valve, comprising an outer stem portion, a flange and an inner stem portion providing an openable slit, all made of soft rubber vulcanized in one piece. The air valve also has a barbed metal tube which is anchored in the soft rubber vulcanized material stem 10 and guides air to the openable slit for inflating and deflating the tire. The air valve is designed for being firmly mounted to the tire.

U.S. Pat. No. 5,694,969 by DeVuyst discloses a self-closing valve in combination with a pressure relief valve. The self-closing valve serves for inflating and deflating the tire via passageways, which laterally bypass the pressure relief valve. When the self-closing valve is unthreaded and removed, the tire is deflated via the passageways. The pressure relief valve serves for releasing overpressure from the tire to the outside via horizontal relief openings, which bypass the self-closing valve. Thus, both valves are arranged functionally in parallel to each other. U.S. Pat. No. 3,442,316 by McMaster discloses an innertube valve stem for tubeless and tubed tires which use Schrader type valves. The valve stem consists of an elongated tapered elastomer body into which the Schrader valve is molded. The valve stem has an elastic snap fit to the tire rim and is replaceable as a whole.

In the prior art, valve stems for tubeless wheels normally have a valve stem body and a valve stem core, which is arranged inside of the valve stem body, as well as a lock nut to secure the valve body on a wheel's rim. The valve stem body is sealed with the valve stem core.

In tubeless wheels often a sealant (also called sealing liquid, sealing agent or sealing fluid) is used to improve gas/air tightness of the wheel. In order to maintain gas tightness over time, a tubeless wheel always has to contain a minimum amount of sealant. Due to dehydration, diffusion and leakage the amount of sealant usually decreases over time. However, it is still unclear how the amount of sealant in an inflated tire can accurately be determined and/or adjusted.

It is an object of the present invention to provide a valve stem system and a method to operate such a valve stem system, which avoids the problems known from the prior art.

SUMMARY OF THE INVENTION

The invention provides a valve stem system for a wheel, especially a wheel with a tubeless tire attached to a rim.

In principle the valve stem system comprises a normally tubular valve stem body with a first end and a second end. In a mounted position the valve stem body extends across the rim wherein the second end of the valve stem body is located in the tire/rim-volume and the first end is arranged outside.

In a variation of the invention a special first valve is arranged at the second end of the valve stem body and hence also at least partially located in the tire/rim-volume, when the valve stem system is mounted on the wheel. The first valve is a self-sealing one-way valve (it may also be called a self-sealing check valve) which is operable although a sealant is present.

A valve stem system according to the present invention allows to insert a measurement device, or other type of device, from outside into the first end of the valve stem system and protrude the valve stem body and subsequently also the first valve element until the measurement device at least partially reaches the tire/rim-space, while the tire essentially still being inflated without substantial loss of pressure. The measurement device may e.g. be a probe, such as a test tube or rod. According to the invention, the first valve element prevents or limits the escape of pressurized air from the tire/rim-volume prior to the insertion as well as during and after the insertion of the measurement device. Hence in contrast to the valve stem systems known from the prior art, a measurement device can be inserted into the tire/rim-space without first having to remove all pressure-maintaining elements of the valve, such as a valve stem core. Hence pressure in the tire/rim-space can essentially be maintained when a measurement device is inserted. Such a valve stem system according to the invention can also be used to add sealant to or remove sealant from the tire/rim-space, while the tire still being under pressure.

Embodiments of the first valve or valve element (both terms being equivalent) will be explained herein after in more detail.

In some embodiments, the first valve may have at least one sealing lip and at least one slit. By displacing or deforming the at least one sealing lip, the at least one slit may be opened or, vice versa, closed. Said sealing lip may preferably be formed and arranged such that the gas pressure gradient between inside and outside of the tire/rim-space exerts a force on the sealing lip. A higher pressure inside of the tire/rim space than outside will typically result in a tighter closing of the slit, while a higher pressure outside of the tire/rim-space will result in an opening of the slit. The latter may e.g. be the case when inflating a tire.

For some applications, the first valve may have at least two sealing lips and at least one slit, the sealing lips extending in converging relationship to each other. Thus a particularly good sealing may be obtained.

In some embodiments, the first valve may comprise a duckbill-type valve, hence have at least two sealing lips and one slit. The two sealing lips may be shaped symmetrically to each other with respect to a plane of symmetry defined by the slit. This allows an improved closing and opening of the slit as well as increased prevention of leakage of pressurized air when protruding the first valve with a measurement device, respectively probe.

In some embodiments, the first valve is integrally formed and comprises an outer sealing face which can be used to seal the gap between valve stem body and the opening where the valve stem protrudes the rim.

The first valve may be made of at least one elastic material, such as a rubber or a silicone material or a similar material. However, the invention is not limited to this selection of material and also other materials or a combination of different materials can be used for the first valve. In some embodiments of the invention the first valve may be integrally made in an injection molding process.

In some embodiments, the valve stem system may further comprise at least one annular sealing element arranged at the second end and inside of the valve stem body or inside of the first valve. The annular sealing element may be integrally formed at the first valve which will simplify the assembly and consequently reduce the production cost of a valve stem system. However, it may also be separated from the first valve. Said annular sealing element has an inner diameter which is slightly smaller than the outer diameter of a measurement device, respectively probe, which will protrude the first valve. Hence it may provide additional sealing against leakage of air during the insertion of a measurement device or probe. In particular, it will reduce the escape of pressured air at the moment e.g. a probe or measurement device starts to protrude the first valve and e.g. the slit of a duckbill-valve starts to open. However, the inner diameter of the annular sealing element should not be too small, so that other elements can be arranged or injected inside the valve stem.

Alternatively, or in addition at least one annular sealing element may also be arranged at the first end of the valve stem body and/or between the first and the second end of the valve stem body and having an inner opening of diameter d.

Alternatively, or in addition a measurement device comprises a sealing element that hinders the escape of air from the rim/tire space when being the measurement device is inserted in the valve stem body. Such a sealing element may be an annular sealing element arranged on the outer surface of the measurement device.

Hence in a valve stem system according to the invention it is possible to insert a probe into the valve stem through the first valve into the tire/rim-space for determining the amount of sealant present. In a variation of the invention it is further possible to fill new sealant or remove surplus sealant through the valve stem and the first valve into the tire without deflating the tire, as will be explained in further details below.

In some embodiments of the invention a second valve may be arranged in the valve stem for example, to provide a further sealing or to ease deflating the tire. Such a second valve may e.g. be any type of valve stem core known from the prior art, such as a Schrader-type or Presta-type core. The second valve may be operatively connected to the first valve. In some embodiments, the second valve is operatively connected to the first valve by a venting element which extends through the valve stem body and is able to open the first valve. This has the advantage, that the tire can be deflated directly by operating the second valve without additional means. Such operative connection may e.g. be obtained using a tube-shape venting element, which can be inserted into the valve stem body and which will open the first venting element, e.g. open a slit, when being pressed against it. A tubular venting element therefore may comprise at least one venting opening arranged on a sidewall, so that the air flowing into the inside of the venting element can flow through the venting opening into the valve stem body.

In a variation of the invention the valve stem body may have a low length if compared to conventional valve stem systems in order to obtain a valve stem system with a particularly compact design. Such a variation may be advantageous in order to prevent damage to the valve stem system (e.g. by vandalism) and/or for aesthetic purposes. Such a variation becomes possible as a second valve may be omitted due to sealing as provided by the first valve.

A further advantage of the valve stem system according to the invention is that the first valve prevents leakage of pressurized air out of an inflated tire while allowing high flow rates into the tire. Such high flow rates are required for the initial inflation of tubeless tires. In the systems known from the prior art, a second valve usually has to be removed from the valve stem prior to the initial inflation, in order to get sufficient air flow rates. After the inflation, the second valve has to be screwed into the valve stem again almost instantly in order to prevent critical depressurizing. This procedure requires fast response and skillful handling. Thanks to the first valve according to the invention, such depressurizing after initial inflation is avoided and hence a second valve (if needed) can be positioned without haste.

If appropriate the first valve may form a thickening at the second end of the valve stem body such that the outer diameter of the first valve is greater than the diameter of the valve stem body. Thus the outer surface of the first valve may be used in order to obtain sealing between the valve stem system and the rim. Good results may be obtained if the first valve comprises a conical or pyramidal (or similarly shaped) outer face. With such a variation, proper sealing contact with the periphery of the valve bores of many types of rims can be established. Therefore, a wide range of wheels/rims may be easily retrofitted with such a variation of a valve stem system. Alternatively, or in addition, the first valve may be designed to precisely fit the interior profile of a specific rim, respectively valve bore.

Alternatively, or in addition, the valve stem body may be designed in order to establish a sealing contact with the rim.

In addition, the first valve usually will prevent sealant from entering into the valve stern. In the valve stem systems known from the prior art, such pollution of the valve stem regularly causes malfunctions of the valves due to so-called valve clogging.

In some embodiments of the invention, the valve stem system may also comprise an end cap. Such an end cap may protect the inner part of the valve stem body from pollution. Alternatively, or in addition it may also provide additional protection from leakage of pressurized air. The cap may e.g. be screwed onto the valve stem body or onto a second valve (if present).

In order to determine the amount of sealant inside of the tire/rim-space, according to the invention a special probe may be provided. Said probe comprises a tubular element and a rod. Said tubular element is made of an at least partially optically transparent material and has a first tube opening at a first tube end and a second tube opening at a second tube end and a tube wall. The rod has a first rod end and a second end. The second rod end is moveably arranged in the tube and can move from a first position to a second position. The distance from the second rod end to the second tube end is in the second position greater than it is in the first position. An orifice is provided in the tube wall. There is an essentially continuous opening between the orifice and the second tube end when the second rod end is at the second rod position. The essentially continuous opening between the orifice and the second rod end is disrupted when the second rod end is at the first rod position.

By furnishing the tubeless wheel with a valve stern system according to the present invention and applying the probe, the remaining amount of the sealant in the tire can be easily and precisely tested without releasing the air pressure or even removing the tire. The probe is made long enough to reach to the bottom of the tire through the valve stem body and the first valve. The orifice should be arranged at a proper position in the tube wall, at least higher than the minimum sealant level in the tire, when the probe is inserted in the sealant and the second tube end reaches the bottom of the tire. Hence it can be determined if a tire contains a predefined minimum amount of sealant. Good results may be obtained if the orifice is arranged higher than the maximum sealant level as thus a wide range of possible sealant levels can be accurately measured.

A retaining element may be arranged at the first rod end and stops the moving of the second rod end in direction of the second tube end at the first rod position (p1). The retaining element serves on the one hand as a holding element to hold the rod, on the other hand as a stopper to limit the moving range of the rod in the tube.

In some embodiments, the rod comprises a first probe sealing element, said sealing element seals the tube in longitudinal direction and is arranged at the second rod end. In some embodiments, the first probe sealing element essentially has a shape of for example, an o-ring or a drop or a bung. However, it is not limited to these types of shape. The first probe sealing element may also be a fluid with a high viscosity, such as a grease.

In some embodiments, a second probe sealing element may be provided and arranged on the rod and located between the first probe sealing element and the first rod end. The second probe sealing element may be an O-ring or a sleeve that is arranged on the rod. The second probe sealing element may also be a fluid with a high viscosity, such as a grease. Such a second probe sealing element helps to prevent pressurized air from flowing through the orifice and tube when the rod is in the first position.

In some embodiments, at least one probe graduation is marked on the outer surface of the tube. When the tube is made of an at least partly transparent material, the amount of sealant remaining in the probe is visible to the user. By providing the graduation marked on the outer surface of the tube, a precise amount of sealant can be estimated or directly read by the user. Such information may be used in order to determine the amount of supplemental sealant that has to be added in order to obtain an optimum amount of sealant. The amount of sealant to add may e.g. be determined using the graduation in combination with information about the type or geometry of the tire.

In some embodiments, the rod may comprise means for indicating the first rod position and/or the second rod position so that the user can better control the rod position during sealant level testing.

In some embodiments, the tube has an outer diameter which is greater than the inner diameter of the annular sealing element to ensure the sealing between the tube and the annular sealing element.

In some embodiments, the second tube end is tapered, so that protrusion of the tube through the first valve is improved. In addition, a tapered second tube end may prevent sealing between the second tube end and the tire. Thanks to the tapered tube end a gap between the second tube end and the tire is left open when the tube is pressed against the tire and thus tire sealant can flow into the tube.

A first variation of a method to test the amount of sealant in a wheel furnished with the valve stem system of the present invention, may comprise the following steps: Removing the second valve, if present; protruding the valve stem body and first valve with the probe until the second tube end reaches the tire, the second rod end being at the first rod position; moving the second rod end to the second rod position so that the orifice allows an equalization of the air pressure between inside and outside the tube which causes a sealant column in the tube; moving the second rod end to the first rod position; pulling the probe out of the valve stem body; comparing the sealant column with the probe graduation. Thanks to this process the sealant level inside the tube and the sealant level outside the tube become equal in the tire, due to the moving the second rod end to the first position again, the sealant column in the tube subsequently is prevented from moving up or down in the tube. In order to determine the sealant level accurately a wheel will usually first be rotated around its axis of rotation until the valve stem system is at the bottom most position of the wheel.

As a further aspect of the invention, as an independent inventive concept, a shifting mechanism for a probe is provided, which allows convenient and reliable measurements of the amount of sealant in a wheel. Such a shifting mechanism can be interconnected with the first tube end and with the first rod end of the probe and provides a first configuration in which the rod is in the first position and a second configuration in which the rod is in the second position.

If desired, such a shifting mechanism may be arranged in a housing which may be connected to the first tube end.

Good results may be achieved if the shifting mechanism switches from the first configuration to the second configuration when a first external force and/or torque is applied to the shifting mechanism. Thus leveling of the column in the probe's tube can be initiated. Therefore, the shifting mechanism may comprise at least one button which can be pressed in order to apply a force. Alternatively, or in addition the shifting mechanism may comprise a twisting element which can be turned in order to apply a torque.

Good results may be achieved if the shifting mechanism switches from the second configuration to the first configuration when the external force and/or moment is removed. Consequently, the sealant column in the tube is prevented from moving up or down in the tube.

For some applications the shifting mechanism may also switch from the second configuration to the first configuration when a second external force and/or torque is applied to the shifting mechanism.

A simple and reliable shifting mechanism may be achieved using a spring element, as will be described in further detail below.

A first variation of a filling, respectively refilling, assembly for a wheel furnished with the valve stem system of the present invention comprises a syringe, a check valve, an extension element and an applicator element. The applicator element can be inserted into the valve stem body until it opens the first valve. The syringe comprises at least one syringe graduation. In some embodiments of the invention, the applicator element may have an outer diameter which is greater than the inner diameter of an annular sealing element, if present.

A particularly user friendly filling/refilling assembly may be obtained if the extension element is flexible, hence may e.g. be made from an elastic material.

A further independent inventive concept relates to another variation of a filling, respectively refilling, assembly for a wheel with a tubeless tire. Such a refilling assembly comprises a syringe, a stopcock (faucet), an extension element (such as e.g. a hose or tube) as well as an applicator element. In such a variation of the invention, the stopcock can be switched from a closed state, when no fluid can pass the stopcock, to an open state, when fluid can pass the stopcock. Thus the stopcock allows to control when sealant is able to flow from the tire/rim space to the syringe and vice versa. The applicator element may be long enough to be inserted through the valve stem body until it reaches the tire. In such a variation of a refilling assembly, the sealant may be (at least partially) transferred from the tire/rim space into the syringe in order to determine the total amount of sealant as well as to allow for visual and/or mechanical and/or chemical analysis of the sealant. Good results may be obtained if the end of the applicator element that gets in contact with the tire is tapered, such that when the applicator element is pressed against the tire, a gap remains open and thus tire sealant can flow into the applicator element. Depending on the type of sealant used, the applicator element's tube may have a relatively large inner diameter which allows relatively high flow rates even for viscous sealants. After (at least partial) removal of the sealant, additional and/or new sealant may be injected into the tire/rim space again.

Due to the stopcock, the syringe may be disconnected from the applicator element, while the applicator element is still inserted in the valve stem system, respectively the rim/tire space, without significant loss of pressurized air taking place.

Good results may also be obtained using a stopcock that is a three or four way valve. Thus not only sealant, but also pressurized air may be provided by the applicator element.

It will be appreciated that a valve stem system as described above is an independent inventive concept which is useable for tubeless wheels without using a probe and/or filling/refilling assembly as described above. The same holds true for the filling/refilling assembly as well as the probe and shifting mechanism, which all can also be considered as being separate, independent inventive concepts.

As a further aspect of the invention, as an independent inventive concept, a syringe may be used in order to store several components of a refilling assembly. Therefore, the space between the plunger, plunger head, barrel and thumb rest (of the plunger), which in normal syringes usually is void, is used in order to store some components, e.g. a valve stem system and/or an applicator elements and/or a stopcock and/or an extension element. Hence all components needed to fill, control and/or refill sealant can be stored safely.

Good results may be achieved if the plunger comprises holding means upon which a check valve and/or a stopcock and/or the extension element and/or applicator element may be securely fastened to the plunger.

For some purposes, the space between the plunger head, barrel and thumb rest may be divided into several compartments, which may be specifically shaped in order to receive the components that have to be stored.

In a variation of this aspect of the invention, a refilling assembly is provided, the syringe and/or check valve and/or a stopcock and/or the extension element and/or applicator element are dimensioned such that the check valve and/or a stopcock and/or the extension element and/or the applicator element can be stored at least partially within the space between the plunger and the barrel of the syringe.

Alternatively, or in addition, also one or multiple valve stem systems may be stored within the space between the plunger and the barrel of the syringe.

BRIEF DESCRIPTION OF THE DRAWINGS

The herein described invention will be more fully understood from the detailed description of the given herein below and the accompanying drawings, which should not be considered as limiting to the invention described in the appended claims.

DETAILED DESCRIPTION OF THE INVENTION

Figure 1:
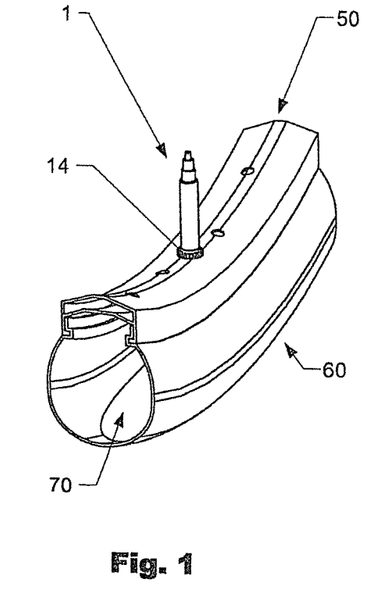
FIG. 1 shows a valve stem system mounted on a rim.

FIG. 1 shows an embodiment of a valve stem system 1 mounted on a wheel rim 50 including with a tire 60 mounted, in particular a tubeless wheel. The tire 60 is filled with sealant 70 for sealing the tire. The valve stem system 1 protrudes outward the outer (centripetal) surface of the rim and is fastened at the rim 50 using a nut 14.

Figure 2:
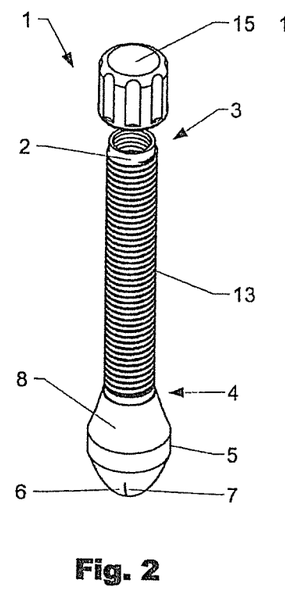
FIG. 2 shows a valve stem system.

FIG. 2 shows an embodiment of a valve stem system 1 comprising a tubular valve stem body 2 and a first valve or valve element 5. The valve stem body 2 has a first end 3 and a second end 4 connected by a passageway which extends in longitudinal direction through the valve body 2. A cap 15, which can be threaded at the first end 3 of the valve stem body 2, is provided. The cap 15 protects the inner volume of the valve stem body 2 from pollution as well as it may serve as an additional sealing element to prevent the passage of pressurized gas through the valve stem body 2. The first valve 5 is arranged at the second end 4 of the valve stem body 2, hence it is arranged at the base of the valve stem system 1. The first valve 5 comprises an outer sealing face 8 as well as sealing lips 6. The two sealing lips 6 form a half-spherical essentially convex shape. In between the two sealing lips 6 there is the valve opening, which in this embodiment is a slit 7. The slit is in a closed state when the two sealing lips 6 are in contact. The sealing lips 6 extend in converging relationship to each other leading to an opening of the slit 7. On its outer surface, the valve stem body has an outer thread 13 which can be used to fasten the cap 15 or attach the valve stem system 1 to a rim e.g. by a nut.

Figure 3:
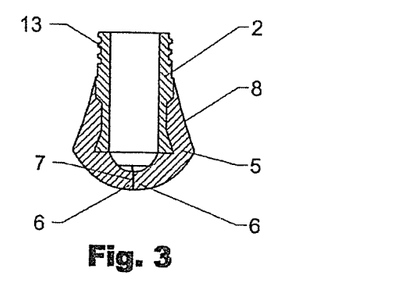
FIG. 3 shows a section view of a valve stem body and a first valve.
Figure 4:
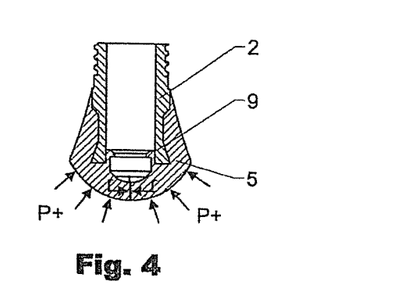
FIG. 4 shows a section view of a valve stem body and a first valve.

FIG. 3 and FIG. 4 show two embodiments of a first sealing element 5 of the valve stem system. The first valve 5 is mounted at the second end of the valve stem body by means of an interlocking and/or a glued connection. The outer sealing surface 8 has a tapered shape and is essentially in parallel to a tapered part of the outer surface of the valve stem body 2, which allows for a mechanically advantageous load transmission between valve stem body 2 and rim 50 when mounted. As shown e.g. in FIG. 3, the sealing lips 7 may also have a rather limited extension in longitudinal direction of the valve stem system, resulting in the first sealing element 5 having a rather compact shape. A first sealing element 5 with such a shape may be less exposed to e.g. impacts on the tire resulting from curbs, stones or potholes.

Using a first valve 5 with convex sealing lips 6 helps to increase sealing of the slit 7. As shown in FIG. 4, the gas pressure in the tire/rim space acting on the outer surface of the sealing lips 6, schematically indicated with arrows P+, causes an increased contact force between the two sealing lips 6, schematically indicated with arrows r. This causes a higher contact pressure between the faces inside of the slit 7 and hence a tighter closure of the slit 7. As shown in FIG. 4, an additional sealing element 9 may be arranged at the second end of the valve stern body. As shown in FIG. 4 the additional sealing element may have an annular shape and may be part of the first valve 5, hence be integrally formed with the first valve 5. In contrast to FIG. 4, FIG. 3 shows an embodiment without such an annular sealing element 9.

Figure 5:
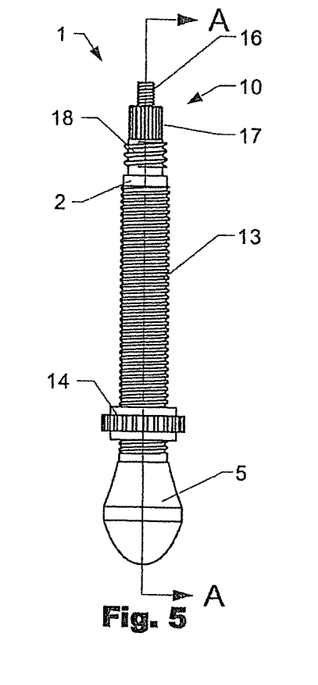
FIG. 5 shows a valve stem system with a second valve mounted.
Figure 6:
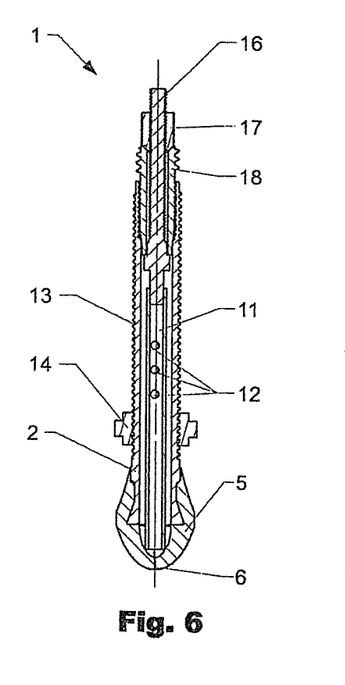
FIG. 6 shows a cross-cut through the valve stem system with a second valve of FIG. 5 along line A-A.
Figure 7:
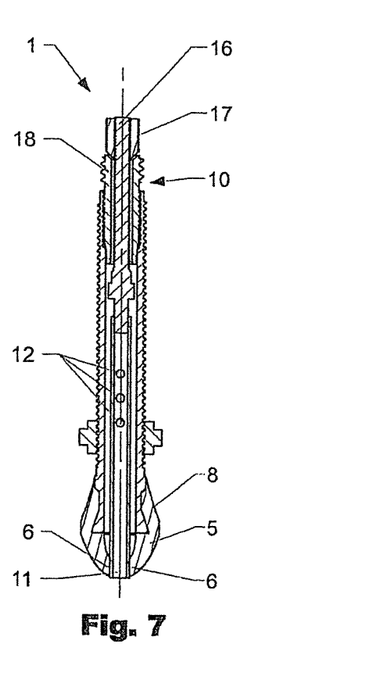
FIG. 7 shows a section view of a valve stem system with a second valve mounted.

FIG. 5 shows one embodiment of the valve stem system (1) with a second valve or valve element 10 mounted removably at the first end 3 of the valve stem body 2, partially housed within the valve stem body 2. The second valve 10 comprises a core rod 16, a core nut 17 and a bushing 18. The second valve 10 may be connected to the valve stem body 2 using a thread, as shown in FIG. 6. The assembling of the core rod 16, the nut 17 and the bushing 18 may be according to, or similar as for Presta-type or Schrader-type valve cores. FIG. 6 is a cross cut of FIG. 5 along line A-A. As can be seen, the core rod 16 has a first end and a second end. In mounted state, said first end may protrude outside of the first end 3 of the valve stem body 2, the second end is located inside of the valve stem body 2. A venting element 11 is arranged at the second end of the valve stem body 2. As shown in FIG. 6, the venting element 11 may have a tubular shape, comprising one or multiple venting openings 12 in its sidewall. Being mechanically operatively connected to the core rod 16, the venting element 11 serves as an extension of the core rod 16. FIG. 7 shows the valve stem system 1 of FIGS. 5 and 6 when inflating or deflating a tire. Therefore, the second valve 10 is unlocked by screwing off the core nut 17, as known e.g. from Presta-type valve cores. After that, the core rod 16 can be shifted towards the first valve 5, causing the venting element 11 to protrude the first valve 5 by opening the slit 7, resulting in a continuous valve opening between the two ends of the valve stem system 1. Consequently, air can continuously flow from the second side of the valve stem system into the venting element 11, through the venting opening 12 into the valve stem body 2 and sequentially through the channel between the bushing 18 and the core rod 16 to the first end 3 of the valve stem system 1, or vice versa in the other direction.

Figure 8:
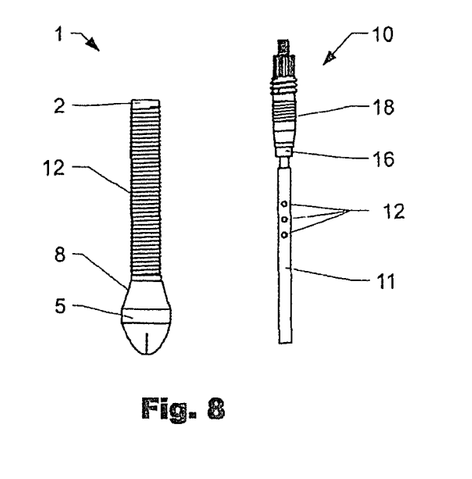
FIG. 8 shows a valve stem system and a second valve.

FIG. 8 illustrates an embodiment of a valve stem system 1 with the second valve 10 being removed from the valve stem body 2.

Figure 9:
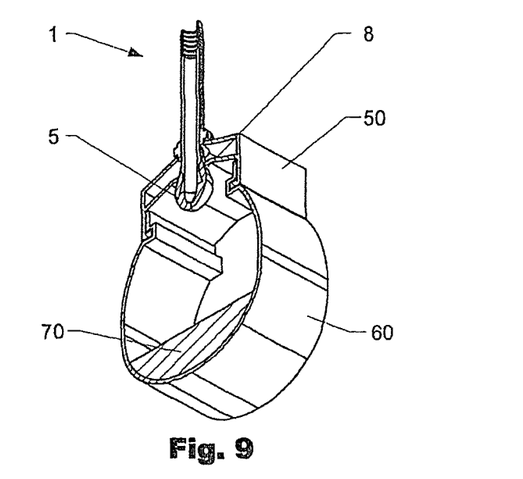
FIG. 9 shows a section view of a valve stem system mounted on a rim.

FIG. 9 shows a section view of the valve stem system 1 when being mounted on the rim. The first valve 5 is essentially located inside of the rim/tire space, preventing the pressurized air from escaping from the rim/tire space.

Figures 10, 11:
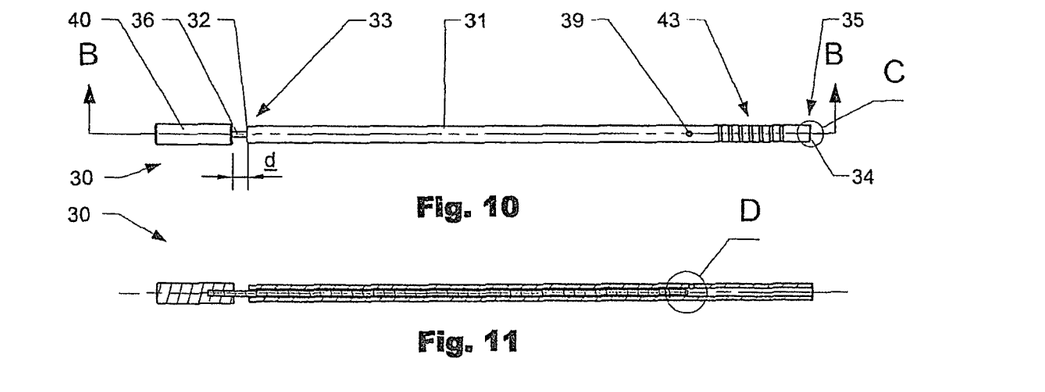
FIG. 10 shows a probe for a valve stem system.
FIG. 11 shows a cross-cut through the probe of FIG. 10 along line B-B.
Figure 17:
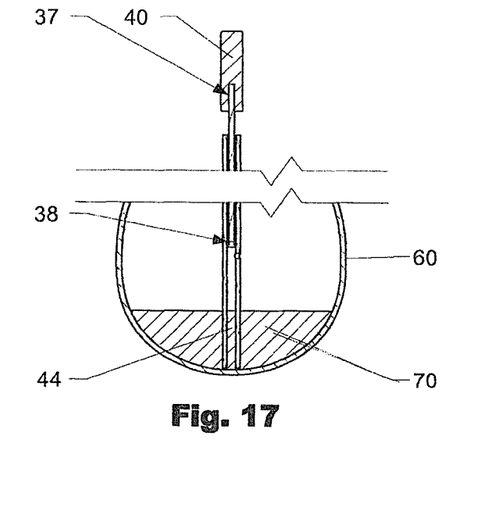
FIG. 17 shows a section view of a probe inserted in sealant.

FIG. 10 shows a probe 30 for testing the amount of the sealant 70 in the tire 60. FIG. 11 shows a section view of the probe 30. The probe 30 comprises a tube 31 with a first tube opening 32 at a first tube end 33 and a second tube opening 34 at a second tube end 35 and a rod 36. The rod 36 has a first rod end 37 and a second rod end 38 as shown in FIG. 17. For testing the amount of sealant, the rod 36 is inserted into the tube 31 and is moveable in the axial direction, whereby the second rod end 38 is located inside of the tube 31. A retaining element 40 is attached to the first rod end 37 as a holding element and as a stopper to prevent the rod 36 from entirely entering into the tube 31. An orifice 39 is arranged in the tube wall to equalize the pressure inside and outside of the tube.

Figure 12:
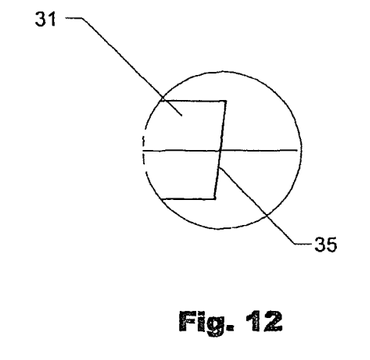
FIG. 12 shows detail C of FIG. 10.

FIG. 12 shows that the second tube end 35 may be tapered, so that the probe can easily go through the first valve 5. In addition, the tapered second tube end 35 ensures that sealant 70 can flow into the tube 31 when the tube 31 is pressed against the tire 60.

Figure 13:
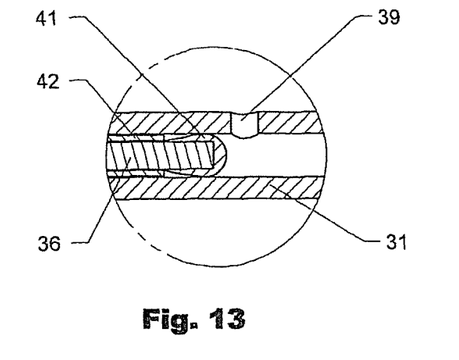
FIG. 13 shows detail D of FIG. 11.
Figure 16:
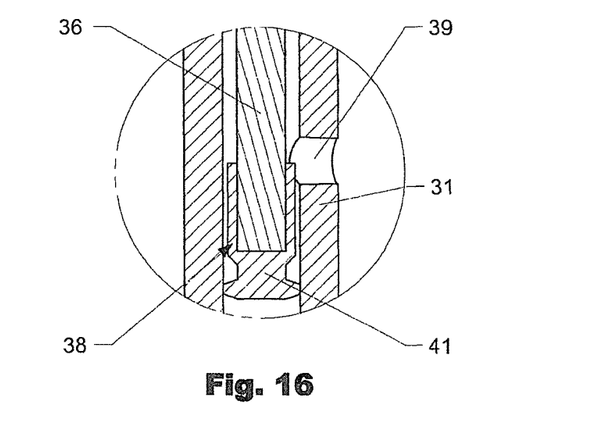
FIG. 16 shows detail E of FIG. 14.
Figure 19:
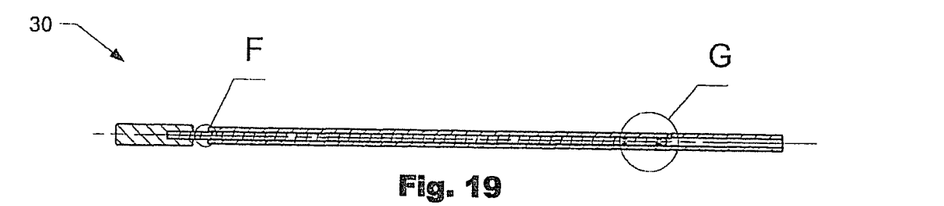
FIG. 19 shows a section view of a probe.
Figure 21:
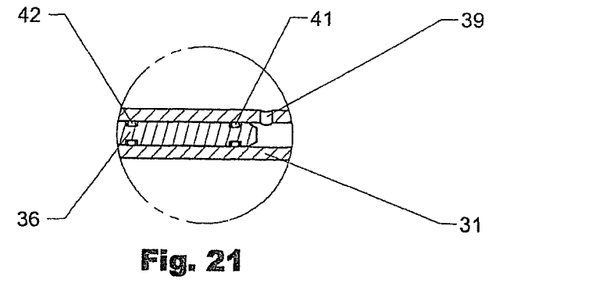
FIG. 21 shows detail G FIG. 19.

FIG. 13, FIG. 16 and FIG. 21 show the probe 30 with a first probe sealing element 41 and a second probe sealing element 42. FIG. 13 shows one embodiment of the probe with the first probe sealing element 41 attached to the second rod end 37 and the second probe sealing element 42 attached to the inner wall of the tube 31. The second probe sealing element 42 may be a tubular element, which can be arranged on the inner wall of the tube 31, for example, by gluing. The first probe sealing element 41 may have a shape of drop or bung. The dimension of the first probe sealing element 41 should be adapted to the inner diameter of the tube 31 by considering the production tolerances to ensure the sealing. The first probe sealing element 41 can be made of elastic material. The second probe sealing element 42 may have a tubular shape. The inner diameter of the second probe sealing element 42 may be adapted to the outer diameter of the rod 36 by considering the production tolerances to obtain a further sealing. FIG. 19 and FIG. 21 show another embodiment of the probe 30 with the first probe sealing element 41 and the second probe sealing element 42 having a shape of o-ring. In this embodiment, the first probe sealing element 41 is arranged near the second rod end 37 and the second probe sealing element 42 is arranged between the first rod end 36 and the second rod end 37. However, the arrangement and the shape of the probe sealing elements 41, 42 are not limited to the variation described above.

Figure 20:
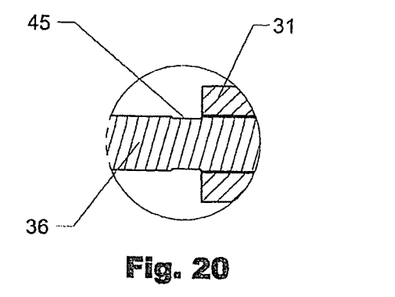
FIG. 20 shows detail F of FIG. 19.

As shown in FIG. 20, a mark 45 is formed or marked on the rod 36 with a position being visible to the user. It allows the user to clearly identify the position of the second rod end 38 relatively to the orifice 39, when inserted in the tube 31.

Figure 14:
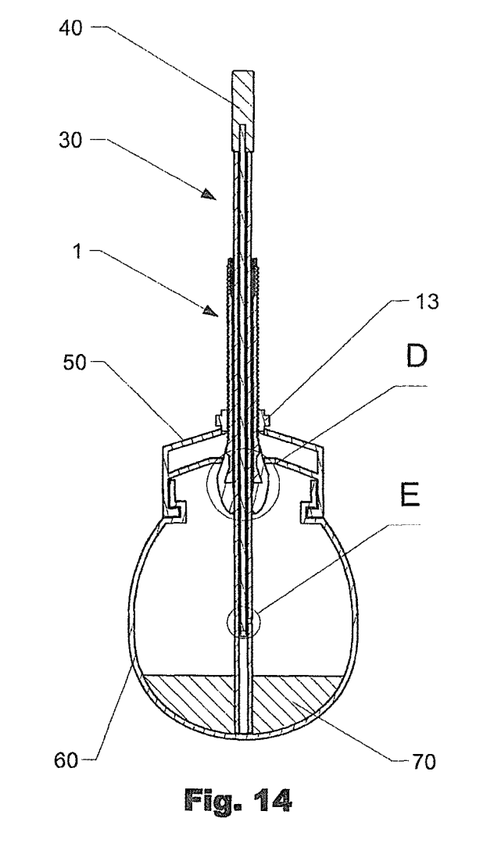
FIG. 14 shows a section view of a probe inserted in sealant.
Figure 15:
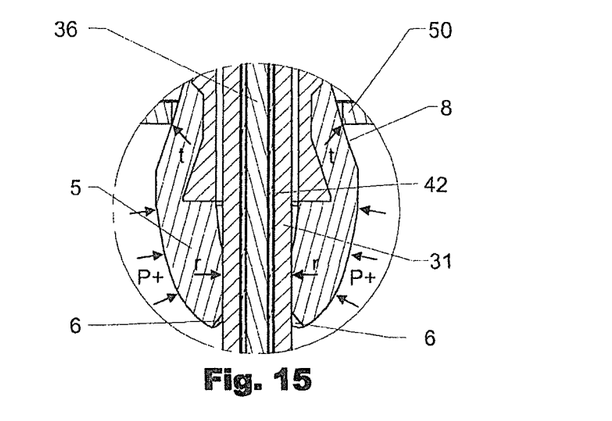
FIG. 15 shows detail D of FIG. 14.
Figure 18:
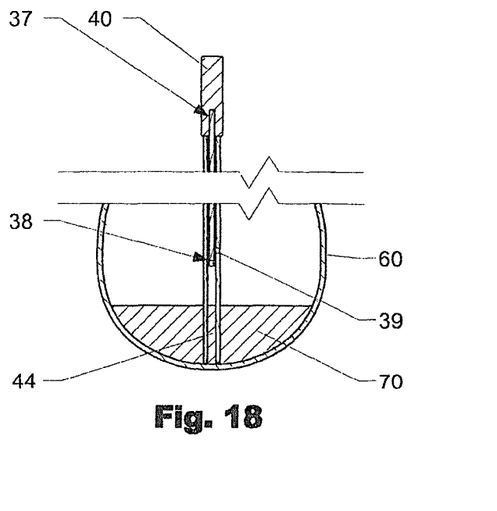
FIG. 18 shows a section view of a probe inserted in sealant.

FIGS. 14 to 17 and FIG. 18 illustrate the process of testing the amount of sealant 70 in the tire 60. In a first step, the retaining element 40 is pushed down toward the first tube end 33 to a position, such that the first probe sealing element 41 is moved to a position below the orifice 39 (FIG. 14 and FIG. 16). The probe 30 is inserted through the slit 7 until the second tube end 35 reaches the tire. Normally, no sealant 70 enters into the tube 30. In a second step, the retaining element 40 is pulled up such that the first probe sealing element 41 is moved to a position above the orifice 39 (FIG. 17). This can be controlled by the user regarding the mark 45 on the rod 36. The sealant 70 enters into the tube 30 and a sealant column 44 has the same height as the sealant outside of the tube 30 in the tire. In a third step, the retaining element 40 is pushed down again toward the first tube end 33 to a position, such that the first probe sealing element 41 is moved to a position below the orifice 39 (FIG. 18). Thus the essentially continuous opening between the orifice 39 and the second tube end 35 is closed which prevents the sealant column from being able to move up or down in the tube 31. The tube 30 can then be removed out of the valve stem body 2 while keeping first probe sealing element 41 staying below the orifice. The amount of the sealant 70 can be read by comparing the sealant column 44 with the probe gradation 43 marked on the outer surface of the tube 30.

Figure 22:
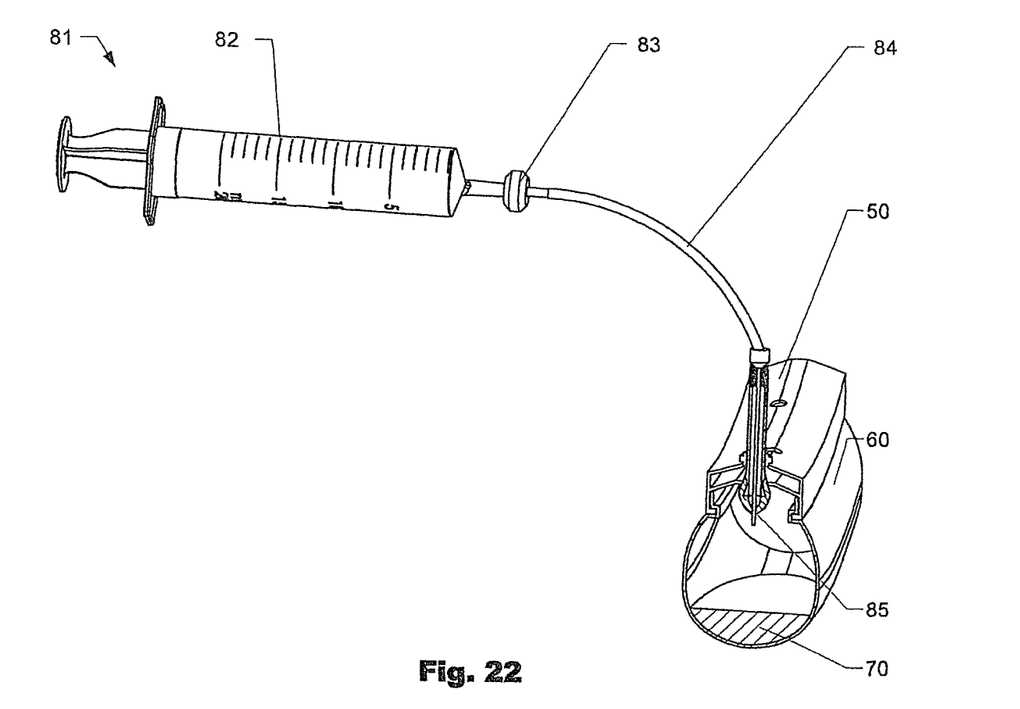
FIG. 22 shows a refill assembly.

FIG. 22 illustrates a refilling assembly 80 for a wheel furnished with the valve stem system of the present invention. The refilling assembly 80 comprises a syringe 81, a check valve 83, an extension element 84 and an applicator element 85. The applicator element 85 can be inserted into the valve stem body 2 until it opens the first valve 5. The syringe comprises at least one syringe graduation 82.

Figure 23:
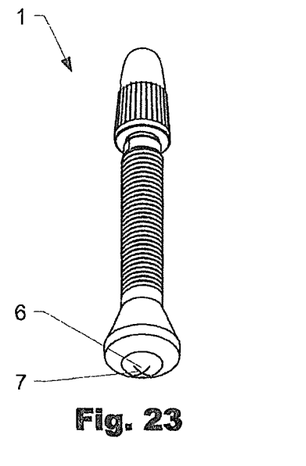
FIG. 23 shows a valve system.
Figure 24:
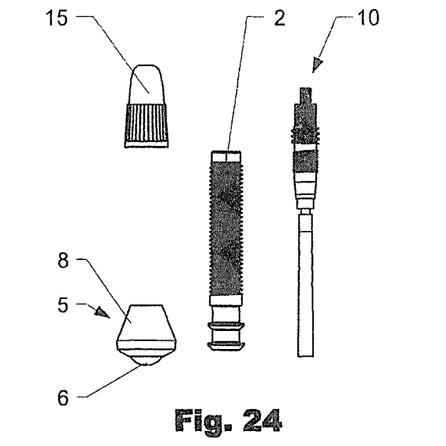
FIG. 24 shows the valve system in partially disassembled state.
Figure 25A:
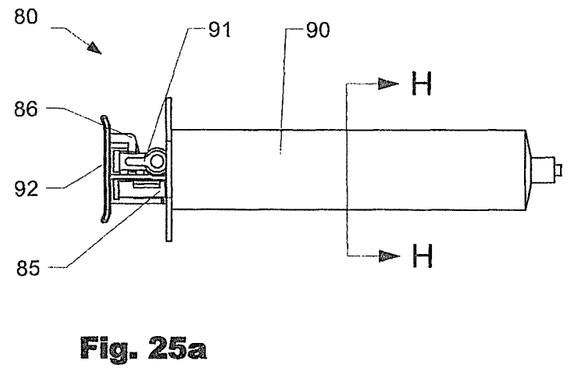
FIG. 25*a* shows a refilling assembly.
Figure 25B:
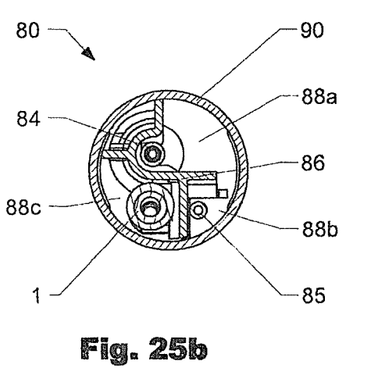
FIG. 25*b* shows cross-section H-H of FIG. 25*a;*

FIGS. 23 and 24 show another embodiment of a valve stem system 1 in assembled, respectively partially disassembled state. As shown, this embodiment of a valve stem system comprises a fist valve 5 that has multiple sealing lips 6.

Figure 26:
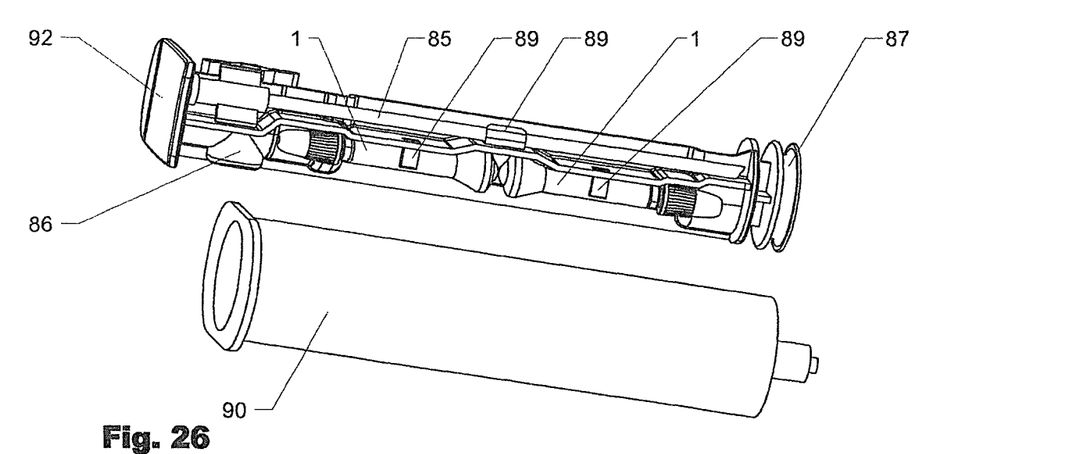
FIG. 26 shows the refilling assembly of FIG. 25a partially disassembled.
Figure 27:
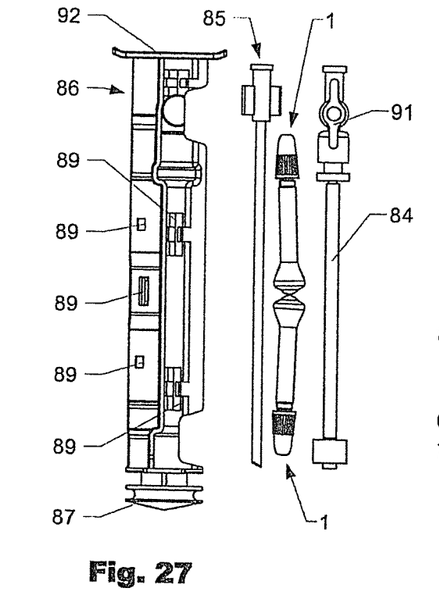
FIG. 27 shows the plunger and the components stored in it.

FIGS. 25a to 27 show a refilling assembly 80 which is designed such that its major components can be stored in a compact way. The refilling assembly 80 comprises a plunger 86 which will usually be positioned within a central opening of a barrel 90, forming a syringe 81. When the plunger 85 is mounted inside of the barrel 90, the space defined by the plunger 85, the plunger head 87, the plunger's thumb rest 92 and the barrel 90 is divided into compartments 88a-c, as can e.g. be seen in FIG. 25b. In the embodiment shown, in a first compartment 88a an extension element 84 of the refilling assembly 80 is positioned, together with a stopcock 91 (not visible in FIG. 25b). In a second compartment 88b an applicator element 85 of the refilling assembly 80 is positioned, as can be seen in FIGS. 25b and 26. In a third compartment 88c, two valve stem systems 1 are positioned, as can be seen in FIGS. 25b and 26. Thus such a variation of a refilling assembly may be sold e.g. for retrofitting a bicycle with new valve stem systems 1 together with a compatible refilling assembly 80. As shown in FIGS. 26 and 27, the shape of plunger 86 may be adapted to the shape of the components that are stored in the compartments 88a-c. Therefore, also holding means 89 may be formed in order to establish a snapping connection with the components for secure storage of them.

Figure 28:
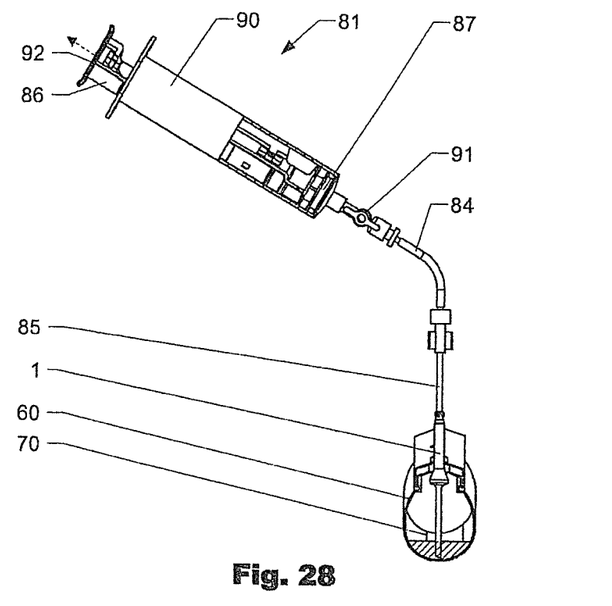
FIG. 28 shows a refilling assembly in a first state.
Figure 29:
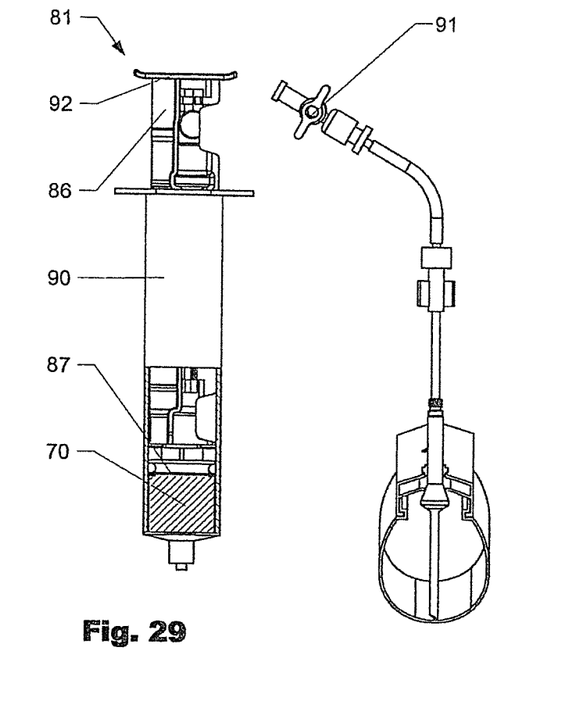
FIG. 29 shows a refilling assembly in a second state.

FIG. 27 also shows an embodiment of a refilling assembly 80 that comprises a relatively long applicator element 85 that has a relatively large inner diameter and a tapered end (lower end in FIG. 27). In addition, this embodiment of a refilling assembly 80 comprises a stopcock 91 that can be switched from a closed state, when no fluid can pass the stopcock 91, to an open state, when fluid can pass the stopcock. As shown in FIG. 28 the stopcock 84 has a first end which can be connected to the syringe 81 and a second end that can be connected to an extension element 84, which in the embodiment shown is a hose. In FIGS. 28 and 29 the barrel's 90 wall has been partially removed for illustrative purposes. As also shown in FIG. 28, the extension element 84 can be connected to the applicator element 85 which can be inserted through a valve stem system 1 into a tire 60. Also in such a refilling assembly 80, the valve stem system 1 successfully prevents pressurized air from escaping from the tire 60 prior to the insertion of the applicator element 85 as well as afterwards. In the embodiment shown, the applicator element 85 is inserted into the valve stem system 1 and hence the rim/tire space until the applicator element's 85 lower tapered end gets into contact with the tire 60. Usually, the stopcock 91 will be in the closed state until this insertion is complete and will then be switched to the open state. Thus the sealant 70 can be transferred to the syringe 81, resulting in a movement of the plunger 86 relatively to the barrel 90, as indicated in FIG. 28 by a dotted arrow. Thus, if wished be the user, essentially all sealant 70 can be removed from the tire 60, as shown in FIG. 29. This transfer may be driven or at least be assisted by the pressurized air in the tire. However, it is clear, that the refilling assembly may also be used after the tire/rim space has been depressurized. A complete removal of sealant 70 will usually be indicated by small air bubbles appearing in the extension element 84 (if it is made from an optically transparent material) and/or the syringe. As soon as the sealant 70 is removed, the stopcock 91 can be switched to the closed state and the syringe 81 may subsequently be disconnected from the stopcock 91 in order to allow for a proper inspection of the sealant 70. Thus by visual, mechanical or chemical means the amount of quality of the sealant 70 can be determined accurately. If needed, the amount of sealant may be adapted and/or it may be replaced by a new sealant 70. Subsequently the syringe 81 can be connected to the stopcock 91 again and the sealant 70 can be injected into the tire 80.

Figure 30A:
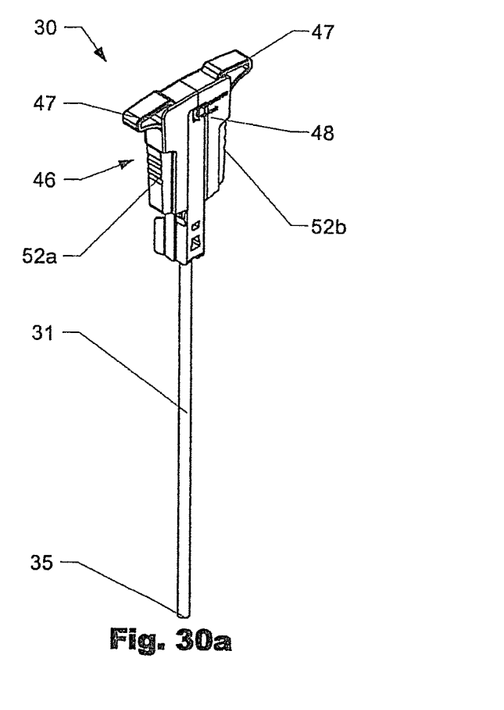
FIG. 30a shows a probe in a perspective view.
Figure 30B:
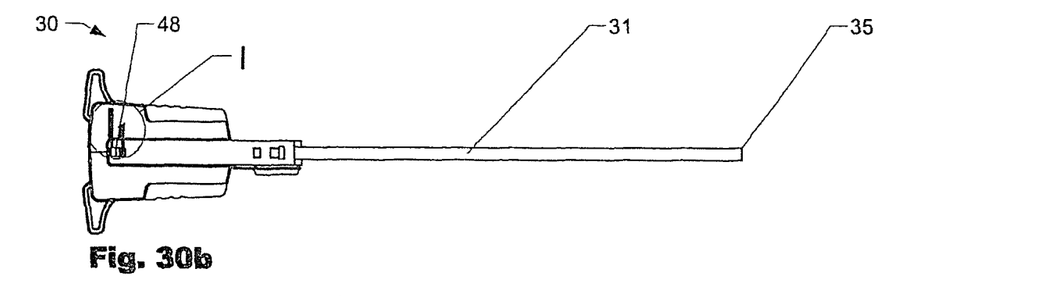
FIG. 30b shows the probe of FIG. 30b in a front view.

FIGS. 30a and 30b show an embodiment of a probe 30 for a valve stem system 1 (not shown) which allows particularly convenient measurements. The probe 30 comprises a tube 31 that has a second tube end 35 which can be inserted in a valve stem system 1. As for the embodiments of probes 30 shown in previous Figures, the tube 31 will usually be made from an optically transparent material. The first tube end (not visible) is arranged in a housing 46. The housing 46 comprises grip elements 47 which allow a convenient handling of the probe 30. The housing further comprises a display opening 48 which displays the position of a rod 36 (not shown) that is arranged inside of the tube 31, as will be explained in further details in FIGS. 31 to 35. The housing 46 shown in FIG. 30a further comprises two lateral buttons 52a, 52b which can be pressed together in order to operate the probe 30, as will be explained in the subsequent figures.

Figure 31:
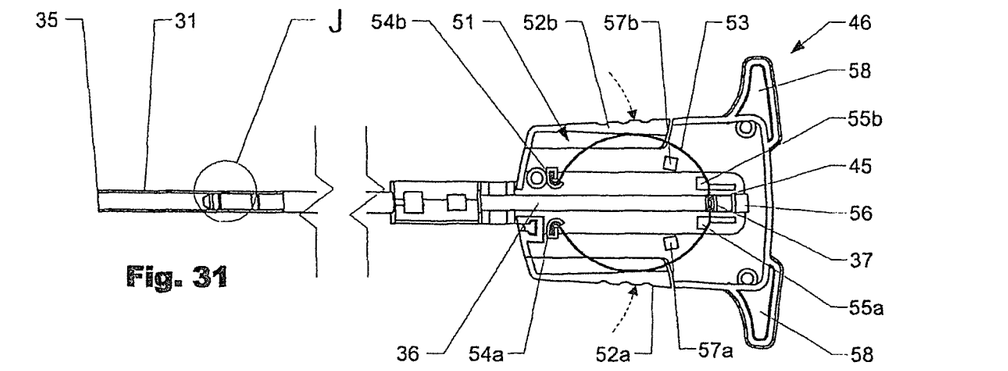
FIG. 31 shows the probe of FIG. 30 in a first state in a back view and broken view, the second tube end being partially removed for illustrative purposes.
Figures 32, 33, 34, 35:
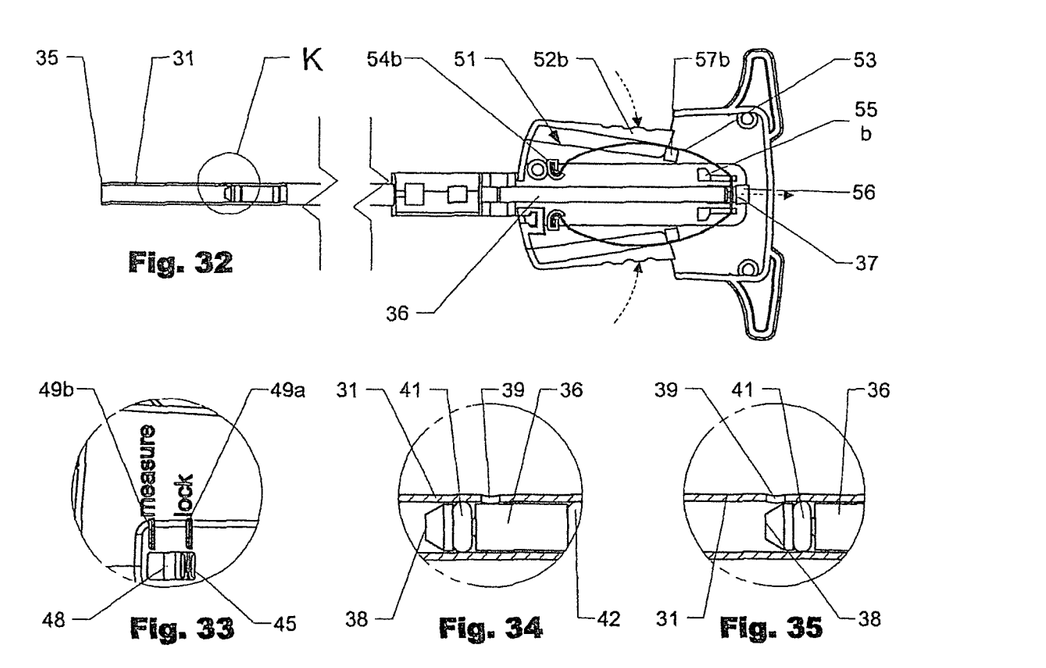
FIG. 32 shows the probe of FIG. 31 in a second state.
FIG. 33 shows detail I of FIG. 30.
FIG. 34 shows detail J of FIG. 31.
FIG. 35 shows detail K of FIG. 32.

In FIG. 31 the inner shifting mechanism 51 of the housing 46 is shown. The shifting mechanism 51 of the embodiment shown comprises a spring element 53 which in this embodiment essentially has the shape of an omega, the two ends of the spring element 53 being fixedly connected to the housing 46 by anchors 54a-b. At a midpoint of the spring element 53 the spring element 53 is connected to the first rod end 37 of a rod 36, said rod being arranged in the tube 31, in a similar way as e.g. shown in FIGS. 10 to 21. The spring element 53 is slightly pre-stressed between the anchors 54a-b and first stoppers 55a-b. The spring is also in contact with the two lateral buttons 52a-b of the housing. The grip element is shown by 58. In FIG. 31 the shifting mechanism 51 is shown in a first configuration, the rod 36 being in a first position, hence the second rod end 38 is in a first distance from the second tube end 35, an orifice 39 in the tube 31 being sealed by a first probe sealing element 41 and a second probe sealing element 42, as shown in detail in FIG. 34. As shown in FIG. 33, in this first configuration, a mark 45 arranged on the first rod end 37 can be seen in the display opening 48 at a first reference mark 49a, indicating to a user that the rod 31 is in a first position with the orifice 39 being separated from the second tube end 35.

As shown in FIG. 32, by pressing the two lateral buttons 52a-b together (indicated by dotted arc arrows) the shifting mechanism 51 can be switched to a second configuration. Therefore, the spring element 53 is laterally squeezed, leading to an elongated shape of the spring element 53 and hence a displacement of the midpoint of the spring element, leading to a displacement of the rod 31 (indicated by the dotted straight arrow). Thus the first rod end 37 can be displaced until it is stopped by a second stopper 56. At the same time, third stoppers 57a-b prevent the two buttons 52a-b, respectively the spring element 53, from being deformed any further. Thus the spring being deformed to a maximum and the rod being displaced to a maximum, it is ensured that the rod is in a second position, as shown in FIG. 35. At this second position, the mark 45 in the display opening 48 would be at a second reference mark 49b (not shown). As shown, the orifice 39 is not separated from the second tube end 35 in this second position, allowing a leveling of the sealant (not shown) inside of the tube 31. As soon as the two lateral buttons 52a-b are not pressed together anymore, the shifting mechanism switches back to the first configuration as the spring element 53 flexes back into its original more circular shape, resulting in the rod 36 moving back to the first position with the orifice 39 being separated from the second tube end 35 again.

What is claimed is:

1. A valve stem system (1) for tubeless wheels, said wheels comprising a rim (50) and a tire (60), said valve stem system (1) comprising:
   a valve stem body (2) with a first end (3) and a second end (4), the second end (4) being located in the tire/rim-volume when mounted on the wheel;
   a first valve (5) comprising a self-sealing one-way valve arranged at the second end (4) of the valve stem body (2); and
   a second valve (10) removably mountable at the first end (3) and, when mounted, at least partially housed in the valve stem body (2), wherein the second valve (10) comprises a valve stem core inserted in the valve stem body (2) and wherein the second valve (10) is arranged in series with respect to the first valve and can be added or removed from the valve stem body (2) while pressure is maintained within the tire/rim-volume by the first valve (5).

2. The valve stem system (1) according to claim 1, wherein the first valve (5) comprises at least one sealing lip (6) and at least one slit (7).

3. The valve stem system (1) according to claim 1, wherein the first valve (5) comprises a duckbill-type valve.

4. The valve stem system (1) according to claim 1, wherein the first valve (5) is formed as a single piece and comprises an outer sealing face (8).

5. The valve stem system (1) according to claim 1, wherein the first valve (5) is made of elastic material selected from the group consisting of rubber and silicone.

6. The valve stem system (1) according to claim 1, wherein the valve stem system (1) further comprises an annular sealing element (9) arranged at the second end (4) and inside of the valve stem body (2) or the first valve (5) and/or at the first end (3) and/or between the first and the second end (3,4) of the valve stem body (2) and having an inner opening with a diameter (d).

7. The valve stem system (1) according to claim 6, wherein the annular sealing element (9) is integrally formed with the first valve (5).

8. The valve stem system (1) according to claim 1, wherein the second valve (10) comprises a Presta-type valve core or a Schrader-type valve core inserted in the valve stem body (2).

9. A valve stem system (1) for tubeless wheels, said wheels comprising a rim (50) and a tire (60), said valve stem system (1) comprising:
   a valve stem body (2) with a first end (3) and a second end (4), the second end (4) being located in the tire/rim-volume when mounted on the wheel;
   a first valve (5) comprising a self-sealing one-way valve arranged at the second end (4) of the valve stem body (2); and
   a second valve (10) removably mountable at the first end (3) and, when mounted, at least partially housed in the valve stem body (2) and operatively connected to the first valve (5) by a venting element (11) which extends through the valve stem body (2) to open the first valve (5), wherein the second valve (10) comprises a valve stem core inserted in the valve stem body (2) and wherein the second valve (10) is arranged in series with respect to the first valve and can be added or removed from the valve stem body (2) while pressure is maintained within the tire/rim-volume by the first valve (5).

10. The valve stem system (1) according to claim 9, wherein the venting element (11) is a tube comprising at least one venting opening (12) arranged on a sidewall.

11. The valve stem system (1) according to claim 9, wherein the second valve (10) comprises a Presta-type valve core or a Schrader-type valve core inserted in the valve stem body (2).

12. Tubeless wheel, comprising a rim (50) and a tire (60), and further comprising a valve stem system (1) according to claim 1, the valve stem system (1) being mounted to the rim (50) of the tubeless wheel.

13. Tubeless wheel, comprising a rim (50) and a tire (60), and further comprising a valve stem system (1) according to claim 9, the valve stem system (1) being mounted to the rim (50) of the tubeless wheel.

\* \* \* \* \*